United States Patent
Hofmann et al.

(10) Patent No.: US 9,623,440 B2
(45) Date of Patent: Apr. 18, 2017

(54) METHOD FOR HYDROPHILIZING SURFACES OF FLUIDIC COMPONENTS AND PARTS CONTAINING SUCH COMPONENTS

(71) Applicant: Roche Diagnostics Operations, Inc., Indianapolis, IN (US)

(72) Inventors: Wolfgang Hofmann, Graz (AT); Taghi Noormofidi, Graz (AT); Doris Zahrl, Graz (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/747,667

(22) Filed: Jan. 23, 2013

(65) Prior Publication Data

US 2013/0136657 A1 May 30, 2013

Related U.S. Application Data

(63) Continuation of application No. PCT/EP2011/062506, filed on Jul. 21, 2011.

(30) Foreign Application Priority Data

Jul. 23, 2010 (EP) .................... 10170613

(51) Int. Cl.
*B05D 5/00* (2006.01)
*B01L 3/00* (2006.01)
*G01N 33/543* (2006.01)

(52) U.S. Cl.
CPC .......... *B05D 5/00* (2013.01); *B01L 3/502707* (2013.01); *B01L 2200/12* (2013.01);
(Continued)

(58) Field of Classification Search
CPC ................ B01L 3/502707; B05D 5/00; G01N 33/54393
(Continued)

(56) References Cited

U.S. PATENT DOCUMENTS

| | | | |
|---|---|---|---|
| 4,358,423 A | 11/1982 | Nedetzky | |
| 4,752,426 A | 6/1988 | Cho | |

(Continued)

FOREIGN PATENT DOCUMENTS

| | | |
|---|---|---|
| EP | 0379156 B1 | 7/1990 |
| EP | 1595605 B1 | 11/2005 |

(Continued)

OTHER PUBLICATIONS

International Search Report issued Aug. 17, 2011 in Application No. PCT/EP2011/062506, 3 pages.

(Continued)

*Primary Examiner* — Dennis M White
*Assistant Examiner* — Bryan Kilpatrick
(74) *Attorney, Agent, or Firm* — Woodard, Emhardt, Moriarty, McNett & Henry LLP

(57) ABSTRACT

A method for at least partially applying a hydrophilic polymer to a measurement channel of a sensor cartridge is provided, which sensor cartridge can be replaceably inserted in an analyzer. The measurement channel comprises at least one sensor element. The method comprises inserting the sensor cartridge into the analyzer, introducing an aqueous solution containing chitosan or a chitosan derivative into the measurement channel of the sensor cartridge, and following a residence time replacing the aqueous chitosan solution with a gaseous or liquid medium, wherein residues of the chitosan or chitosan derivatives remain on the inside surface of the measurement channel and hydrophilize the surface.

17 Claims, 2 Drawing Sheets

(52) U.S. Cl.
CPC .. *B01L 2300/0627* (2013.01); *B01L 2300/161* (2013.01); *G01N 33/54393* (2013.01)

(58) Field of Classification Search
USPC ............. 206/569; 422/68.1, 554; 427/8, 230
See application file for complete search history.

(56) References Cited

U.S. PATENT DOCUMENTS

| | | | |
|---|---|---|---|
| 5,578,073 | A | 11/1996 | Haimovich et al. |
| 2002/0128234 | A1* | 9/2002 | Hubbell et al. ............... 514/100 |
| 2005/0176678 | A1* | 8/2005 | Horres et al. .................... 514/54 |
| 2005/0230767 | A1 | 10/2005 | Park et al. |
| 2009/0130746 | A1 | 5/2009 | Cao |
| 2009/0176314 | A1* | 7/2009 | Steinboeck et al. .......... 436/174 |

FOREIGN PATENT DOCUMENTS

| | | |
|---|---|---|
| EP | 2067848 A1 | 6/2009 |
| EP | 2077452 B1 | 7/2009 |
| EP | 2105735 B1 | 11/2014 |
| JP | 2004294231 | 10/2004 |
| JP | 2005-345463 | 2/2005 |
| JP | 2005-288717 A | 10/2005 |
| JP | 2006-292472 A | 10/2006 |
| JP | 2006-337249 | 12/2006 |
| JP | 2008-170351 A | 7/2008 |
| JP | 2008249449 A | 10/2008 |
| JP | 2009520209 A | 5/2009 |
| JP | 2009162756 A | 7/2009 |
| WO | 01/47637 A1 | 7/2001 |
| WO | 2006/127451 A3 | 11/2006 |
| WO | 2009/062940 A1 | 5/2009 |
| WO | WO 2010/040047 A2 | 4/2010 |

OTHER PUBLICATIONS

English translation of JP 2008-170351 A, published Jul. 24, 2008, 14 pages.
Huang, Xiaojia et al., Preparation and evaluation of stable coating for capillary electrophoresis using coupled chitosan as coated modifier, Talanta, 2006, 463-468, 69.
Yao, Y. J. and Li, S. F. Y., Capillary zone electrophoresis of basic proteins with chitosan as a capillary modifier, Journal of Chromatography, 1994, 97-104, 663.
English Abstract of JP2004294231.
English Abstract of JP2005288717.
English Abstract of JP2005345463.
English Abstract of JP2006292472A.
English Abstract of JP2006337249.
English Abstract of JP2008249449A.
English Abstract of JP2009162756A.
English Abstract of JP2009520209A.
Koev, Stephan t. et al., "Mechano-transduction of DNA hybridization and dopamine oxidation through electrodeposited chitosan network", The Royal Society of Chemistry, 2007, 7, pp. 103-111.
Lu, Xiao Ying et al., "Evaluation of Protein Adsorption on Chitosan Surfaces with Relfectomerty Interference Spectroscopy", Sensors 2001, 1, pp. 148-160.
Luo, Xiaolong et al, "In situ generaton of Ph gradients in microfluidic devices for biofabricaiton of freestanding, semi-permeable chitosan membanes", The Royal Society of Chemistry 2010, 10, pp. 59-65.
Park, Jung Jin et al., "Chitosan-mediated in situ biomolecule assemply in complete packaged microfluidic devices", The Royal Society of Chemistry 2006, 6, pp. 1315-1321.

* cited by examiner

METHOD FOR HYDROPHILIZING SURFACES OF FLUIDIC COMPONENTS AND PARTS CONTAINING SUCH COMPONENTS

CROSS-REFERENCE TO RELATED APPLICATIONS

This application is a continuation of International Application No. PCT/EP2001/062506, filed 21 Jul. 2011, which claims the benefit of European Patent Application No. 10170613.3, filed 23 Jul. 2010, the disclosures of which are hereby incorporated by reference in their entirety.

BACKGROUND

Especially when determining gaseous analytes ($O_2$, $CO_2$) in aqueous fluids problems may arise in sample measurement or calibration or quality control, if the sample or the calibrating or quality control medium does not completely fill the fluid carrying region of the sensoric element, or if gas bubbles, for instance air bubbles, are present in this region. Gas bubbles are likely to occur if the measurement channel of the sensor cartridge has non-uniform inner surfaces, which have differing wetting properties with fluids. Gas bubbles will most frequently arise or adhere at sites of the measurement channel where the wetting properties of the inner surfaces of the fluidic components or parts change discontinuously. This will for instance be the case when surfaces of different materials meet. The measurement channel usually comprises a multitude of fluidic parts made of different materials whose adjoining surfaces have different hydrophilic or hydrophobic qualities and thus different wetting properties.

U.S. Pat. No. 4,358,423 already mentions the problem of enclosed air bubbles which distort measurement results, since the bubbles impede sufficient wetting of the surface of the sensor element used. Measures for detecting such distortions must be taken especially in the case of automated analyzers where the filling process of the measurement capillary or the absence of bubbles in the measurement chamber must be monitored. The patent cited proposes to solve the problem by a method in which the electrical resistance between at least two points in the measurement chamber is measured and the filling process of the measurement chamber is controlled depending on the resistance value measured.

European Pat. No. 0 379 156 B1 describes coating methods, in which first a polyisocyanate solution is applied to the surface of a medical instrument (in particular a catheter), then the solution is (optionally) dried and subsequently a solution of a polymer containing carboxylic acid is applied. Such two- or multi-step methods with a plurality of agent solutions and chemical reactions usually require many process steps, which at the user site are not feasible at all or only at great cost.

Coating of surfaces of medical implants, catheters and pacemakers with layers containing chitosan is for instance known from U.S. Pat. No. 5,578,073, where it is used to reduce the risk of thrombosis when such devices of medical technology are introduced into the human body. The layer consists of chitosan and an additional, biologically active component, for instance PVA or serum albumin, which is embedded in a chitosan membrane. Such layers are not suitable for measurement channels with sensor elements, however.

In U.S. Pat. No. 4,752,426 there is described a method for hydrophilization of surfaces, in which chemically reactive groups or radicals are formed on the surface by means of a low-temperature plasma treatment. Subsequently a monomeric solution is applied to the surface. The monomers will chemically react with the chemically active groups or radicals on the surface, thus finally forming on the surface a coating by graft polymerization. This method has the disadvantage that the process steps must be carried out by the manufacturer and must be very precisely coordinated. The plasma treatment parameters for instance must be carefully chosen so that only such chemically reactive groups or radicals will be formed on the surface that can act as nuclei for subsequent graft polymerization.

In European Pat. No. 1 595 605 B1 the wetting problem is solved by providing a fluidic system (e.g., a sensor cartridge) for an analyzer, which comprises one or more fluidic parts (e.g., measurement channel) and at least one sensor element, where a film of hydrophilic polymer is applied on the inner surfaces of these parts without any intervening layers. The inner surface of the fluidic system is first given a physical-chemical pre-treatment. Subsequently the inner surfaces of the parts are brought into contact with a solution of the hydrophilic polymer, and then the solution is replaced by a gaseous medium, the surfaces remaining wetted by a part of the solution. Upon removal of the solvent a film of hydrophilic polymer is finally formed on the inner surfaces. This relatively complicated coating method can only be carried out at the manufacturing site.

From U.S. Pat. Appln. Pub. No. 2009/0130746 A1 there is known a factory-based method for coating the inner surfaces of a microchannel system, whose aim is to avoid non-specific adsorption of reagents in PCR-analysis. Here solutions containing chitosan or chitosan derivatives are used. The microchannel system of the chips is filled with a 5% solution of chitosan and covered by mineral oil. A 12 hour heat treatment at 75° C. follows. After removal of the chitosan solution the microchannels are flushed with a solvent, water and a buffer solution. The method is not suitable for measurement channels containing sensor elements.

In many applications it would, however, be of advantage if coating or hydrophilization of the inner surfaces of the measurement channel were not exclusively done at the manufacturing site, since hydrophilization should take place immediately before (or during) the actual use of the cartridge in an analyzer to avoid aging effects. If aqueous solutions are used for surface treatment at the manufacturing site, individual sensor elements might prematurely react with the aqueous solution and the sensor element might be activated by taking in water ("wet up" of the sensor)—an effect which would be undesirable.

It would also be conceivable to use a highly effective detergent in one of the operational fluids to obtain sufficient hydrophilization. Despite the undoubted efficacy of this measure, its use in the context of the present disclosure is not indicated due to undesirable side effects.

SUMMARY

It is against the above background that the embodiments of the present disclosure provide certain unobvious advantages and advancements over the prior art. In particular, the applicants have recognized a need for improvements in methods for hydrophilizing surfaces of fluidic components and parts containing such components.

The present disclosure relates to a method for at least partially applying a hydrophilic polymer to the measurement channel of a sensor cartridge, which is to be inserted into an analyzer, the measurement channel comprising at least one sensor element. The present disclosure further relates to a fluidpack, which can be replaceably inserted into an analyzer, and which comprises at least one container for operating fluids needed in using the analyzer, such as rinsing, calibrating and/or quality control fluids for the analyzer, and further to a sensor cartridge, which can be replaceably inserted into an analyzer, whose inner surfaces of the fluidic components, in particular the measurement channel containing at least one sensor element, are at least partially coated with a hydrophilic polymer.

Although the embodiments of the present disclosure are not limited to specific advantages or functionality, it is noted that the present disclosure provides a sensor cartridge with hydrophilized surfaces of the measurement channel to avoid formation of gas bubbles or adherence of gas bubbles during filling with aqueous operational fluids or sample fluids, hydrophilization being carried out by the user immediately prior to or during use of the sensor cartridge in the analyzer.

In accordance with one embodiment of the present disclosure, a method for at least partially applying a hydrophilic polymer to the inner surfaces of a measurement channel of a sensor cartridge is provided, which sensor cartridge is configured to be replaceably inserted into an analyzer, the measurement channel comprising at least one sensor element, the method comprising: (a) inserting a sensor cartridge into the analyzer; (b) introducing an aqueous solution containing chitosan or a chitosan derivative into the measurement channel of the sensor cartridge, the chitosan or chitosan derivative having a degree of deacetylation between about 10% and about 100%, typically between about 50% and about 100%, and especially typically between about 70% and about 95%; and (c) replacing the aqueous solution containing the chitosan or chitosan derivative after a certain residence time with a gaseous or liquid medium, whereby residues of the chitosan or chitosan derivative remain on the inner surface of the measurement channel and on parts of the at least one sensor element bounding the measurement channel, and hydrophilize the inner surface and the parts bounding the measurement channel.

The method may be applied at the user site—without any pretreatment—in a simple way, typically in the form of an automated routine of the analyzer.

To improve hydrophilization steps (b) and (c) may be performed repeatedly.

According to an embodiment of the present disclosure, it is also possible to apply steps (b) and (c) to refresh hydrophilization of sensor cartridges that are already in use, either at certain intervals of time or following a certain predetermined number of analyte determinations and/or calibration or quality control procedures, the steps being initiated either automatically or manually.

According to another embodiment of the disclosure, the use of chitosan or a chitosan derivative for fabricating an insular or complete coating of the inner surfaces of fluidic components of sensor cartridges, in particular of the inner surfaces of a measurement channel containing at least one sensor element. It has been found unexpectedly that a chitosan layer on sensor elements will not impair sensor function, in particular if the layer is applied in islands or as a monolayer. The parts of the sensor elements in contact with the lumen of the measurement channel form an integral part of the wall of the measurement channel and are coated with a chitosan layer together with the other parts of the measurement channel, in accordance with the present disclosure. If in the context of the present disclosure the term measurement channel is used for better legibility, it is to be understood that according to the embodiments this comprises also the parts of the sensor elements in contact with the lumen of the measurement channel, which form an integral part of the wall of the measurement channel. It has furthermore been found that even an island coating which does not cover the entire surface will already cause an improvement of the hydrophilic surface properties.

In the context of the present disclosure the term "sensor elements" is to be understood as designating all devices by means of which physical or chemical parameters of a fluid can be determined and which are in direct contact with the sample to be analyzed. Examples are for instance electrochemical or optical sensors for determining gas values, pH, ionic values and metabolite values of blood samples. Sensor elements usually comprise one or more layers of organic and/or inorganic substances, typically polymers, which are applied to a carrier substrate differing from the substances, on the side of the measurement channel facing the fluid sample.

These and other features and advantages of the embodiments of the present disclosure will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present disclosure.

DETAILED DESCRIPTION

The data given mostly refer to variants using a chitosan solution for hydrophilization.

Chitosan is a polyamine saccharide derived from chitin. If the molecule contains an increased amount of deacetylated 2-amino-2-desoxy-β-D-glucopyranose units, it is named chitosan. A linear polymer will result, which usually consists of about 2000 monomers. Chitosans with fewer or more monomer units are known, however, and are also covered by the present disclosure.

The pKa value of a typical chitosan is approximately 6.5 depending on pH-dependent protonation or deprotonation of the amino groups of the chitosan molecule. This means that at low pH (below the pKa value) the majority of amino groups is positively charged, making the chitosan molecule easily soluble in water (polycation). This also explains the typical solubility of chitosans in acids.

At higher pH values the percentage of protonated amino groups decreases. This means that at pH values above the pKa value of chitosan the majority of amino groups is not charged and the chitosan molecule is less soluble in water.

Figure 2:
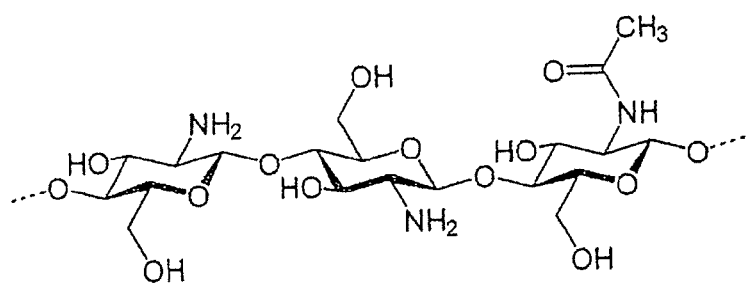
FIG. 2 illustrates the structural formula of chitosan.

In FIG. 2 there is shown a typical segment from the structural formula of a chitosan molecule. The chitosan shown is in the deprotonated state, i.e., the amino groups are not charged. This state occurs primarily at increased pH values.

The pH-dependence of chitosan solubility acts in a positive way on the precipitation of the chitosan, since replacement of the weakly acidic chitosan solution in the measurement channel by an operational fluid of slightly alkaline pH creates a slightly alkaline environment which positively affects the precipitation of the polysaccharide.

The present disclosure also permits the use of chitosan derivatives besides pure chitosans.

Chitosan derivatives as specified by the present disclosure are derivatives of chitosan in which the hydrogen atoms of the OH-groups are at least partly replaced by low-molecular substituents. Typical possible substituents according to the disclosure are —$CH_3$(methyl), —$CH_2$—$CH_3$(ethyl), —$CH_2$—$CH_2$—$CH_3$(n-propyl), —$CH(CH_3)_2$(isopropyl), —$CH_2$—O—$CH_3$(methoxymethyl) and —$CH_2$—O—$CH_2$—O—$CH_3$, —$CH_2$—$CH_2$—OH(hydroxyethyl), —CO—$CH_3$(acetyl). Replacement of the hydrogen atoms of the OH-groups by one or more of these substituents may occur in all or only in some of the OH-groups of the chitosan.

Figure 3:
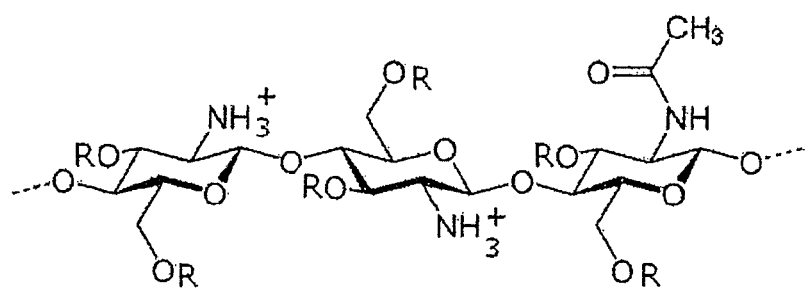
FIG. 3 illustrates the structural formula of chitosan derivatives according to the present disclosure.

Chitosan derivatives according to an embodiment of the present disclosure are shown in FIG. 3.

FIG. 3 shows a typical segment from the structural formula of a chitosan (the case in which all R are hydrogen atoms) or of a chitosan derivative, where the R's represent low-molecular substituents, either partly different or of the same type, from a group comprising —H, —$CH_3$, —$CH_2$—$CH_3$, —$CH_2$—$CH_2$—$CH_3$, —$CH(CH_3)_2$, —$CH_2$—O—$CH_3$, and —$CH_2$—O—$CH_2$—O—$CH_3$, —$CH_2$—$CH_2$—OH, —CO—$CH_3$. The chitosan derivative shown here is in the protonated state, i.e., the amino groups are positively charged —$NH_3^+$ groups. This state occurs primarily at lowered pH-values.

When in the context of the present disclosure the terms chitosan or chitosan derivatives are used for the sake of simplicity, it is to be understood that the above described chitosan derivatives and solutions of these chitosan derivatives are subsumed.

Figure 1:
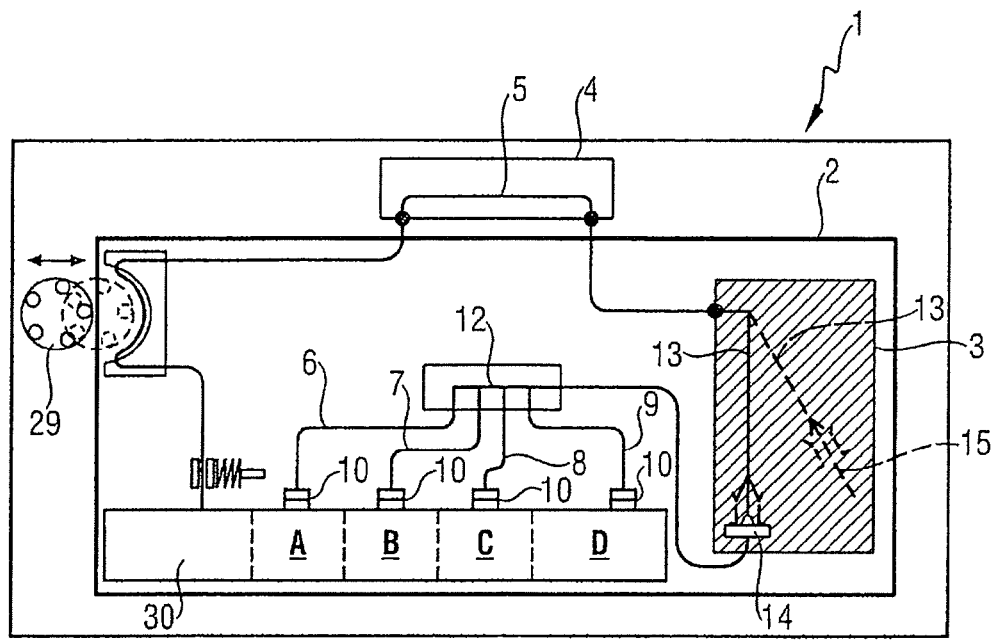
FIG. 1 is a schematic drawing of an analyzer with inserted fluidpack (reagent cartridge) having a plurality of containers for operational fluids and for a chitosan solution.

The schematically shown analyzer 1 of FIG. 1 for analysis of medical sample fluids, for instance blood samples, has a reagent cartridge or fluidpack 2, which can be exchangeably inserted into the analyzer. In the fluidpack 2 there is disposed a number of containers A to D configured as reagent bags containing operational fluids, such as calibrating, quality control and rinsing fluids, which may optionally be fed to an input unit 3 and subsequently to a measurement channel 5 with at least one sensor element, the channel being located in a sensor cartridge 4. The input unit 3 of the analyzer 1 is provided with a tiltable input element 13 (for instance a hollow needle), which in its base position connects to a docking element 14 for supplying calibrating and rinsing media, while in a position 15 tilted outwardly from the base position, sample fluids may be introduced. Sample input may occur from different vessels (e.g., syringe, capillary, glass vessel, etc.)

In the present example one of the rinsing, calibrating, or quality control fluids in containers A to C additionally contains chitosan, or the fluidpack 2 has yet another container D for a typically aqueous chitosan solution. This variant is typical since it permits automatic execution of the process disclosed herein. Alternatively it is also possible to feed the chitosan solution into the measurement channel of the sensor cartridge in another way, for instance by aspiring a chitosan containing solution via the input element 13 of the analyzer.

Each reagent bag A to D has a multi-way valve 10 (bag valve) directly at the entrance of each connecting line 6, 7, 8, 9, each valve being controlled by the analyzer and having at least two valve positions, the first valve position establishing a fluid connection between the respective connecting line 6, 7, 8, 9 and the corresponding reagent bag A to D. In the second valve position the respective reagent bag A to D is closed off and a connection to ambient air is opened. All connecting lines 6, 7, 8, 9 of the reagent bags A to D departing from the multi-way valves 10 open into a common collecting line 12, which leads to the docking element 14 of the sample input unit 3.

Downstream of the sensor cartridge 4 the fluid line passes the fixed part of a peristaltic pump 29 integrated in the analyzer 1 and finally opens into a waste bag 30 located in the reagent cartridge or fluidpack 2.

To sum up, the following solutions are available:
- a chitosan-containing solution, typically of physiological pH-value, is provided, typically in the fluidpack of the analyzer (which is on hand anyway)
- a method is provided for the at least partial coating of the inner surfaces of the measurement channel with chitosan shortly before or during the use of the sensor cartridge
- a sensor cartridge is provided where for hydrophilization the measurement channel and other fluidic components of the sensor cartridge have an insular or complete coating of the inner surfaces, which coating consists of chitosan or contains chitosan. This is also the case for chitosan derivatives.

In order to coat the inner surfaces of the measurement channel with chitosan the measurement channel is first filled with an aqueous chitosan solution, which is then replaced by a gaseous medium (air). Residues of chitosan remain on the inner surfaces of the measurement channel and the sensor elements.

Alternatively, the measurement channel is first filled with an aqueous chitosan solution, which is then replaced by a solution having a higher pH-value than the chitosan solution, for instance a slightly alkaline operational fluid (calibrating, rinsing or quality control fluid) of the analyzer. Due to the increase in pH the protonated amino groups of chitosan are deprotonated and the number of positive charges decreases. This causes a decrease of solubility of chitosan and thus encourages deposition on the inner surfaces of the measurement channel.

Alternatively, the chitosan-containing solution may be supplied via an operational fluid (calibrating, rinsing or QC fluid), by adding chitosan (and optionally other agents, such as buffer substances) to the given contents of the operational fluid.

The aqueous chitosan solution has a pH-value less than about 7, typically a pH-value between about 6.4 and about 6.8.

The surfaces of the measurement channel treated in this way have a surface wettability which is improved for all surfaces forming the measurement channel and is higher than the surface wettability of the inner surfaces of the measurement channel without chitosan coating. Due to the improved and more uniform wettability for aqueous fluids the risk of gas bubble formation or adherence during the filling process with operational or sample fluids is significantly reduced.

In order that the embodiments of the disclosure may be more readily understood, reference is made to the following examples, which are intended to illustrate but not limit the scope thereof.

Experimental Results
Preparation of the Chitosan Solution

Chitosan solution is prepared at the factory in accordance with the following scheme:
- chitosan is dissolved in acid
- a certain pH-value is set by means of buffer agents Mineral acids and all bases may be used as acidic and alkaline components; in order to establish a buffer system it will be of advantage to use organic HEPES-base (as Hepes-Na salt).

As chitosan raw material the product Sigma #448877 (Sigma-Aldrich) is used, which is specified to have a degree of deacetylation between 75% and 100%. The product is further specified by rheological parameters.

In the following example a chitosan was used, which was specified according to the manufacturer to have a deacetylation degree of 82% and a mean molecular weight of 300-400 kda.

The formula shown in Table 1 has for instance been found to be effective (the concentrations given are concentrations of the prepared solution in the final volume).

TABLE 1

| | |
|---|---|
| Chitosan (Sigma #448877, 82% deacetylation, 300-400 kda) | ca. 0.3 g/l |
| NaCl | 49 mmol/l |
| Hepes, free acid | 15 mmol/l |
| Hepes, sodium salt | 3 mmol/l |

The solution may also contain a preservative.

Figure 4:
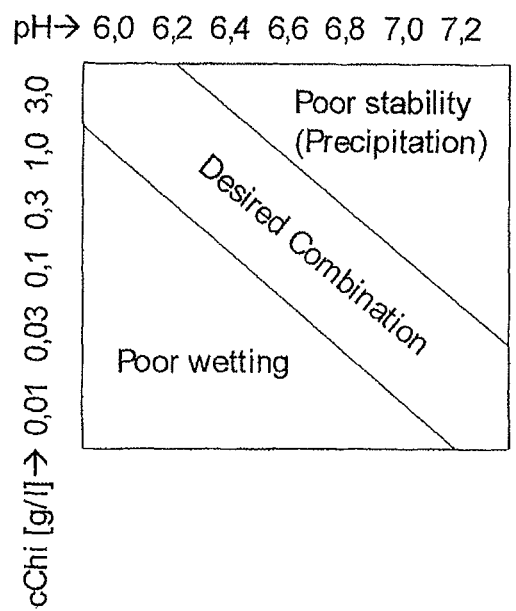
FIG. 4 is a state diagram of a chitosan solution, with pH on the abscissa and chitosan content on the ordinate.

The pH-value of this solution is approximately 6.7. In preparing the recipe it has been found that the applicability of the solution does not only depend on chitosan concentration, but also to a high degree on the pH set. At high pH the solution will become unstable due to precipitation of the polymer. If the pH of the solution is too low coating of the inner surfaces will be insufficient. These dependencies are visualized in the schematic diagram of FIG. 4, with pH-value assigned to the abscissa and chitosan content to the ordinate.

Typically, the chitosan solution is contained in the reagent pack 2 of the analyzer, specifically in the bag-like container D of FIG. 1 (see also, European Pat. No. 2 077 452 B1).

The chitosan solution contained in container D of the fluidpack 2 is aspired into the measurement channel 5 of the sensor cartridge 4 by an automated process and remains there for a residence time of about 5 to 30 seconds, during which the inner surfaces of the measurement channel 5 are at least partially coated with chitosan.

Either the measurement channel 5 is now emptied and the sensor cartridge is (after a certain drying period) ready for its designed use, or the chitosan solution is directly replaced by one of the operational fluids with a somewhat higher pH, the two solutions mixing in a stepwise manner due to the laminar flow. In the context of the present disclosure it has been found unexpectedly that due to the increasing pH-value this mixing has a positive influence on the precipitation of chitosan on the inner surfaces of the measurement channel.

The process of at least partially coating the inner surfaces of the measurement channel of the sensor cartridge with chitosan is carried out prior to the first use or activation of the sensor cartridge.

There is also the possibility of repeatedly performing the process during the "in-use" life of the sensor cartridge, in order to maintain or renew the at least partial coating with chitosan of the inner surfaces of the measurement channel of the sensor cartridge.

It has been found that the wetting effect of chitosan persists at least for a certain period of time. Deposition of the polysaccharide causes a time-limited hydrophilization of the surfaces of the sensor channel.

The data contained in the following Table 2 show the effect of wetting solutions in an exemplary measuring system. A sample channel with a sensor array (see, e.g., International Pat. Appln. Pub. No. WO 2009/062940 A1) is used. Metal contacts are disposed between the sensors, which in normal use serve to determine samples by electrical contacting. The system may also be used to identify air bubbles within the measurement channel (see U.S. Pat. No. 4,358,423).

In the experiment new sensor cartridges have been put to use for the first time. In such cartridges the measurement channel is dry and has not yet had contact with a fluid. A first filling of the sensor channel with a test fluid was carried out. The test fluids used in this case were an operational fluid (A/B), blood (C) or a chitosan solution (D).

The operational fluid used acts as a calibrating fluid and is an aqueous solution of salts and buffer agents with set concentrations of gases ($O_2$/$CO_2$) and a pH-value of 7.35. Monitoring of gas bubbles is carried out during subsequent alternating filling and draining of the sensor channel with operational fluid.

TABLE 2

| Experiment | A | B | C | D |
|---|---|---|---|---|
| Initial Wetting | Initial Wetting by calibration solution | Initial Wetting by calibration solution with tenside Triton x 100 | Initial Wetting by blood | Initial Wetting by chitosan solution pH 6.7 (Sigma #448877, 82% deacetylation, 300-400 kDa) |
| Operational fluid | calibration solution | calibration solution with tenside Triton x 100 | calibration solution | calibration solution |

TABLE 2-continued

| Experiment | A | B | C | D |
|---|---|---|---|---|
| Number of observed cycles | 2071 | 1055 | 829 | 832 |
| Air bubbles detected | 43% | 6% | 20% | 3% |

As shown by the percentages, the tenside additive in the calibration solution causes a drastic reduction of air bubbles (experiment B). The tenside additive cannot be realized at the concentration used in the experiment, however. Initial wetting with blood also has a positive effect (experiment C) on the following filling processes with operational fluid. This is a known effect which probably is due to deposition of certain proteins. Initial wetting with chitosan (experiment D) causes a significant reduction of air bubbles due to polymer deposition. The frequency of air bubble formation is similarly low as in experiment B, although the operational fluid in experiment D does not contain a tenside.

Effects of Different Chitosans on Wetting Behavior of Surfaces by Water

Figures 5A, 5B:
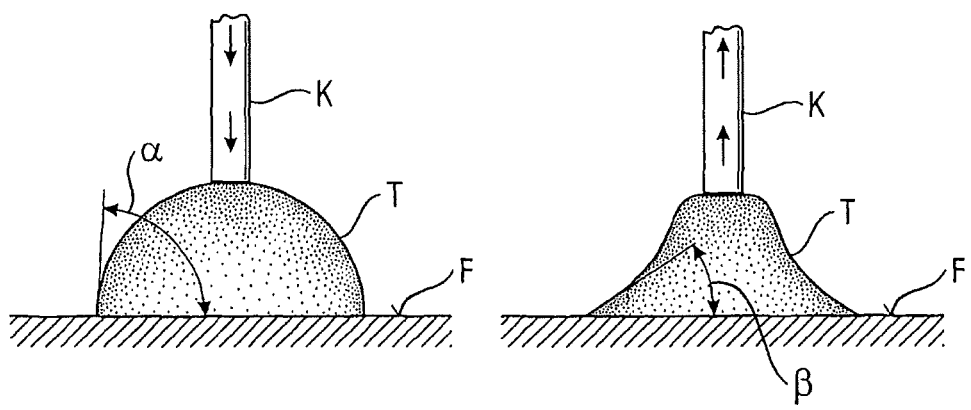
FIGS. 5a and 5b provide a schematic presentation of a measurement arrangement for determining the wetting behavior of a substrate surface.

The effect of treating a substrate surface with a chitosan solution may for instance be judged by measuring its wetting behavior with water. To this end the contact angle of a drop of water on the surface is measured in both the advancing and the receding mode. FIGS. 5a and 5b explain both procedures. Whereas in the advancing mode (FIG. 5a) the "advancing angle" α is determined as a measure, that is the instantaneously arising angle between drop T and surface F when fluid is added via a capillary K, in the receding mode (FIG. 5b) the drop T is partly sucked up and the inertia of the fluid on the surface F is measured by the "receding angle" β. Surfaces treated with chitosan solution exhibit large differences between advancing and receding angle, a behavior which is called contact angle hysteresis and, as a deviation from ideal thermodynamic behavior, is explained by inhomogeneities of surface energies.

It must therefore be assumed that in the described treatment of a measurement channel with a chitosan solution the coating of the initially hydrophobic channel surfaces occurs only partly and in the form of domains or islands. The measurement channel with its sensor elements is almost permanently filled with fluid, however, while the analyzer is in use and thus the retreating behavior is more important for the wetting of the sensors than the advancing behavior. In the following description of various chitosans only the receding angle β is taken into account.

Description of the Experiment

The substrates (polyethylene surface) are dipped into an aqueous solution containing chitosan for 30 seconds. Then the solution is washed off by an aqueous buffer solution (pH 7.3). After drying of the rinsing fluid the surfaces undergo a wetting angle test. The measuring device used is Dataphysics® Contact Angle Systems OCA. The wetting angle is determined in the receding mode. 7 µl of distilled water is applied via a dispenser and 5 µl is then sucked off. The receding angle β of the residual drop T is determined by image processing.

The individual types of chitosan are characterized by degree of deacetylation and molecular weight distribution. Since the latter is very difficult to determine, technical chitosan products make use of a standardized rheological method (viscosity of a one-percent solution in acetic acid). The viscosity value in mPas is used as characteristic and serves as an indirect measure for the mean molecular weight.

The following Table 3 shows the reduction of the receding angle β after the wetting process for diverse chitosans. As reference values the values after wetting by chitosan-free buffer were used. Degrees of deacetylation and ranges of molecular weight are given as specifications. According to the manufacturer the molecular weight ranges given are typical for the mean mole mass of each product.

TABLE 3

| Deacetylation | Molecular weight range | Manufacturer/ product number | Receding angle β on polyethylene |
|---|---|---|---|
| [%] | [kDa] | | [°] |
| 95 | 50-100 | Heppe*/24701 | 38.9 |
| 95 | 300-400 | Heppe*/24706 | 40.5 |
| 95 | 600-800 | Heppe*/24711 | 48.1 |
| 82 | 300-400 | Sigma**/448877 | 48.7 |
| 70 | 300-400 | Heppe*/24206 | 50.7 |
| Substrate (polyethylene) after wetting with chitosan-free solution | | | 95.4 |

*: Manufacturer Heppe Medical Chitosan GmbH, Halle a.d. Saale, Germany
**: this chitosan product is Chitosan Sigma #448877, which was used in the above examples, with a manufacturer-specified deacetylation of 82% and a mean molecular weight of 300-400 kda.

The following Table 4 shows the effect of the wetting procedure on diverse materials, which are typically used in the sensor channel. One of the above wetting solutions was used for the experiments, specifically the solution with Chitosan Sigma #448877 with a manufacturer-specified deacetylation of 82% and a mean molecular weight of 300-400 kda.

TABLE 4

| Surface material | Receding angle β after treatment with chitosan-free solution | Receding angle β after treatment with chitosan solution |
|---|---|---|
| Polyethylene | 94.5° | 48.1° |
| Barex ® | 68.0° | 12.2° |
| Borosilicate glass | 52.5° | <10° |
| Polycarbonate | 65.5° | 25.9° |
| Polyurethane | 83.1° | 27.5° |

Barex ® is an acrylonitrile-methyl acrylate copolymer (ANMA) of INEOS USA LLC, Delaware City, USA (www.ineosbarex.com).

It has thus been shown that typically chitosans in the molecular weight range 50-800 kda and with deacetylation between 70% and 95% are effective, and that the wetting procedure will improve wetting on different materials. In the context of the present disclosure it is also possible, however, to use chitosans or chitosan derivatives with lower or higher molecular weights or lower or higher deacetylation. The molecular weight range may extend from 1 kda to 5000 kda; degree of deacetylation may be between 10% and 100%.

It is noted that terms like "preferably", "commonly", and "typically" are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present disclosure.

It is also noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

It will be apparent to those skilled in the art that various equivalents, changes, and modifications may be made to the embodiments described herein without departing from the spirit and scope of the claimed subject matter. Thus it is intended that the specification cover the modifications and variations of the embodiments described herein provided such modifications and variations come within the scope of the appended claims and their equivalents.

What is claimed is:

1. A method for at least partially applying a hydrophilic polymer to the inner surfaces of a measurement channel of a sensor cartridge, which is configured to be replaceably inserted into an analyzer for analysis of medical sample fluids, said measurement channel comprising at least one sensor element, said method comprising:
    (a) inserting a sensor cartridge into the analyzer;
    (b) inserting a fluidpack, which is configured to be replaceably inserted into an analyzer, into the analyzer, the fluidpack containing an aqueous chitosan solution having a pH-value between about 6.4 and about 6.8 and containing chitosan or a chitosan derivative, said chitosan or chitosan derivative having a degree of deacetylation between about 10% and about 100%, the fluidpack further containing an alkaline operational fluid of the analyzer having a pH value higher than the pH value of the chitosan solution;
    (c) following step (b), introducing a medical sample fluid into the measurement channel of the sensor cartridge received within the analyzer and performing an analysis of the medical sample fluid with the analyzer;
    (d) after step (c), introducing the chitosan solution from the fluidpack into the measurement channel;
    (e) following step (d), replacing the chitosan solution after a residence time with the alkaline operational fluid from the fluidpack, whereby residues of the chitosan or chitosan derivative remain on and hydrophilize the inner surfaces of the measurement channel and the at least one sensor element; and
    repeating steps (c)-(e) following step (e) so as to have steps (d) and (e) repeated at predetermined intervals.

2. The method according to claim 1, wherein the chitosan or chitosan derivative has a degree of deacetylation between about 50% and about 100%.

3. The method according to claim 1, wherein the chitosan or chitosan derivative has a degree of deacetylation between about 70% and about 95%.

4. The method according to claim 1, wherein steps (d) and (e) are repeatedly executed one after the other to improve hydrophilization.

5. The method according to claim 1, wherein the chitosan solution is replaced after a residence time of between about 5 and about 30 seconds.

6. The method according to claim 1, wherein the alkaline operational fluid is a rinsing, calibrating or quality control fluid.

7. The method according to claim 1, wherein the concentration of the chitosan or chitosan derivative in the rinsing, calibrating and/or quality control fluid or the aqueous solution in the separate container is between about 0.03 g/l and about 3 g/l.

8. The method according to claim 1, wherein the concentration of the chitosan or chitosan derivative in the rinsing, calibrating and/or quality control fluid or the aqueous solution in the separate container is about 0.3 g/l.

9. A method for applying a hydrophilic polymer to the inner surfaces of a measurement channel of a sensor cartridge received within an analyzer for analysis of medical sample fluids, the sensor cartridge being configured to be replaceably inserted into the analyzer, said measurement channel comprising at least one sensor element, said method comprising:
    (a) inserting the sensor cartridge into the analyzer, said analyzer including a source of at least one liquid medium and additionally a source of an aqueous chitosan solution containing chitosan or a chitosan derivative, the aqueous chitosan solution having a pH-value between about 6.4 and about 6.8 and the liquid medium having a pH-value higher than the pH value of the aqueous chitosan solution;
    (b) following step (a), introducing a medical sample fluid into the measurement channel of the sensor cartridge received within the analyzer and performing an analysis of the medical sample fluid with the analyzer;
    (c) following step (b), introducing the chitosan solution from the analyzer into the measurement channel of the sensor cartridge and retaining the chitosan solution in the measurement channel for a period of time sufficient to at least partially coat with the chitosan or chitosan derivative the inner surfaces of the measurement channel and the at least one sensor element;
    (d) following step (c), replacing the chitosan solution with said liquid medium, whereby residues of the chitosan or chitosan derivative remain on and hydrophilize the inner surfaces of the measurement channel and the at least one sensor element; and
    repeating steps (b)-(d) after step (d) so as to have steps (c) and (d) repeated at predetermined intervals.

10. The method of claim 9 in which said chitosan or chitosan derivative has a degree of deacetylation between about 10% and about 100%.

11. The method of claim 9 in which the source of the at least one liquid medium and the source of the aqueous chitosan solution is a fluidpack which can be replaceably inserted into the analyzer.

12. The method according to claim 9, wherein the liquid medium used in replacing the chitosan solution is an alkaline operational fluid of the analyzer.

13. The method according to claim 9, wherein the chitosan solution is replaced after a residence time of between about 5 and about 30 seconds.

14. A method of operating a medical sample fluid analyzer including a replaceable sensor cartridge comprising a measurement channel, said method comprising both testing medical sample fluids and periodically hydrophilizing the sensor cartridge, comprising:
    (a) inserting a sensor cartridge into the analyzer, the analyzer including a source of at least one liquid medium and additionally a source of an aqueous chitosan solution containing chitosan or a chitosan derivative, the aqueous chitosan solution having a pH-value between about 6.4 and about 6.8 and the liquid medium having a pH-value higher than the pH-value of the aqueous chitosan solution;
(b) after step (a), introducing a medical sample fluid into the measurement channel and performing an analysis of the medical sample fluid;
(c) after step (b), removing the medical sample fluid from the measurement chamber;
(d) after step (c), introducing the chitosan solution into the measurement channel of the sensor cartridge and retaining the chitosan solution in the measurement channel for a period of time sufficient to at least partially coat with the chitosan or chitosan derivative the inner surfaces of the measurement channel and the at least one sensor element;
(e) replacing the chitosan solution with the liquid medium, whereby residues of the chitosan or chitosan derivative remain on and hydrophilize the inner surfaces of the measurement channel and the at least one sensor element;
(f) removing the liquid medium from the measurement chamber;
(g) after step (f), repeatedly introducing a medical sample fluid into the measurement channel of the sensor cartridge while received within the analyzer and performing an analysis of the medical sample fluid with the analyzer; and
(h) repeating steps (c)-(g) so as to have steps (d)-(f) repeated at predetermined intervals.

15. A method of refreshing the hydrophilicity of the inner surfaces of a measurement channel of a sensor cartridge after use by a medical sample fluid analyzer of the sensor cartridge to analyze a medical sample fluid, said analyzer including a source of at least one liquid medium and additionally a source of an aqueous chitosan solution containing chitosan or a chitosan derivative, comprising:
(a) introducing the chitosan solution from the analyzer into the measurement channel of the sensor cartridge and retaining the chitosan solution in the measurement channel for a period of time sufficient to at least partially coat with the chitosan or chitosan derivative the inner surfaces of the measurement channel and the at least one sensor element;
(b) replacing the chitosan solution with the liquid medium, whereby residues of the chitosan or chitosan derivative remain on and hydrophilize the inner surfaces of the measurement channel and the at least one sensor element, the chitosan solution having a pH-value between about 6.4 and about 6.8 and the liquid medium having a pH-value higher than the pH-value of the chitosan solution;
(c) introducing a medical sample fluid into the measurement channel of the sensor cartridge received within the analyzer and performing an analysis of the medical sample fluid with the analyzer; and
(d) repeating steps (a)-(c) so as to have steps (a)-(b) repeated at predetermined intervals.

16. The method according to claim 1, wherein the chitosan solution is a rinsing, calibrating or quality control fluid.

17. The method according to claim 9, wherein the chitosan solution is a rinsing, calibrating or quality control fluid.

* * * * *